United States Patent [19]

Boyd

[11] Patent Number: 5,636,823
[45] Date of Patent: Jun. 10, 1997

[54] INTERIOR DRAG BRAKE FOR TELESCOPING TUBES

[75] Inventor: Howard Boyd, Oldenburg, Ind.

[73] Assignee: Hill-Rom Company, Inc., Batesville, Ind.

[21] Appl. No.: 380,126

[22] Filed: Jan. 30, 1995

Related U.S. Application Data

[62] Division of Ser. No. 869,001, Apr. 15, 1992, Pat. No. 5,400,995.

[51] Int. Cl.⁶ .................................................. F16M 11/00
[52] U.S. Cl. ........................... 248/414; 248/407; 277/165
[58] Field of Search ........................ 188/381, 322.18; 277/165, 29; 248/414, 407

[56] References Cited

U.S. PATENT DOCUMENTS

| | | | |
|---|---|---|---|
| 2,915,349 | 12/1959 | Gomberg | 277/165 |
| 3,149,849 | 9/1964 | Baldridge | 277/165 |
| 3,227,497 | 1/1966 | Heckethorn | 277/29 |
| 3,268,235 | 8/1966 | Jacobellis | 277/165 |
| 3,814,445 | 6/1974 | Bitzan | 277/165 |
| 4,098,515 | 7/1978 | Sakata | 277/165 |
| 4,174,843 | 11/1979 | Arena et al. | 277/165 X |
| 4,337,956 | 7/1982 | Hopper | 277/29 |
| 4,601,310 | 7/1986 | Phillips | 277/165 X |
| 4,637,458 | 1/1987 | Hernandez | 277/165 X |
| 5,040,905 | 8/1991 | Boyd | 277/165 X |
| 5,159,814 | 11/1992 | Jakobsson | 277/165 X |

FOREIGN PATENT DOCUMENTS 2072798  10/1981  United Kingdom .............. 188/322.18

*Primary Examiner*—Korie Chan
*Attorney, Agent, or Firm*—Barnes & Thornburg

[57] ABSTRACT

An IV pole having an interior drag brake which selectively prevents downward movement or allows downward movement of the pole due to gravitational acceleration including a first pole member and at least a second pole member which telescopes into and out of the first pole member. The second pole member includes on its lower end an O-ring encircling the end, and a nylon split collar encircling the O-ring. In another embodiment, a seal is disposed between the first and second pole members and is operable to create an air cushion beneath the second pole member and within the first pole member. The seal can be an O-ring seal, a Quad-Ring® seal or a lip seal. A valve is disposed in the first pole member for bleeding off air between the first and second pole members, whereby the second pole member has a predetermined or selectively controllable rate of descent with respect to the first pole member.

13 Claims, 2 Drawing Sheets

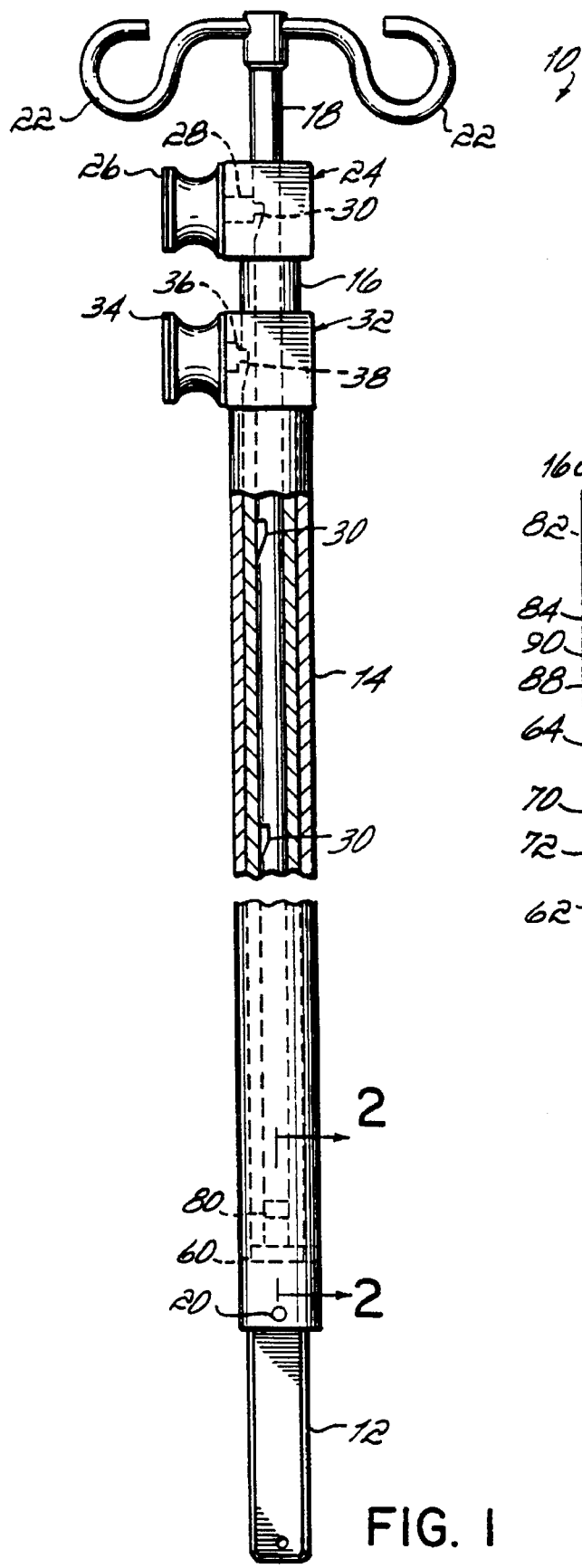
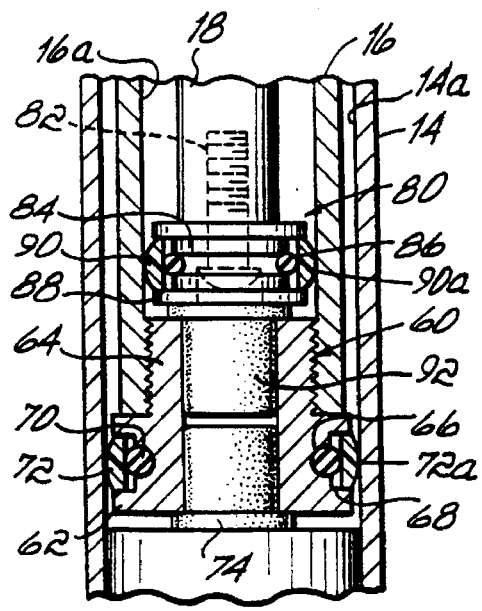
FIG. 2
FIG. 1

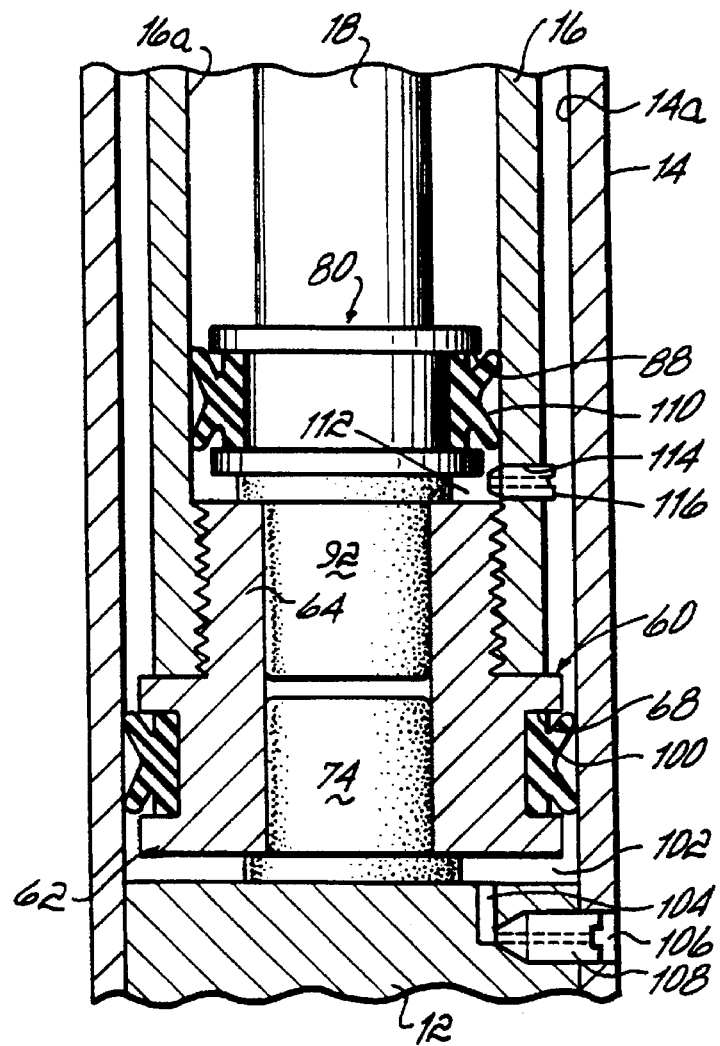
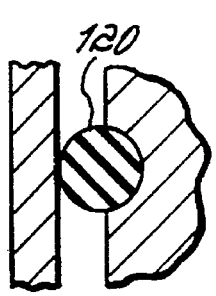
FIG. 4A
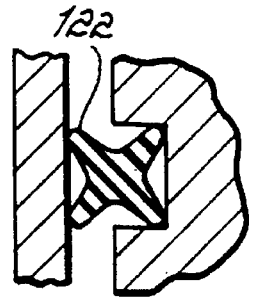
FIG. 4B
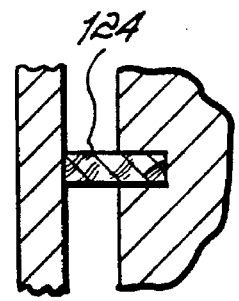
FIG. 4C
FIG. 3

1

INTERIOR DRAG BRAKE FOR TELESCOPING TUBES

This is a divisional of application Ser. No. 07/869,001 filed Apr. 15, 1992, now U.S. Pat. No. 5,400,995.

FIELD OF THE INVENTION

This invention relates to IV poles, and more particularly to an IV pole including an interior drag brake therein for selectively preventing free fall or allowing a controlled rate of descent of the pole and IV bags supported thereby due to gravitational acceleration.

BACKGROUND OF THE INVENTION

IV poles currently in existence have two or more pole sections which telescope to provide for height adjustment of bags of IV solution supported by the IV pole. Typically the outer pole includes a spring loaded pin mechanism which fits into one of several detents in the inner telescoping pole. When the spring loaded pin is retracted from the detent, the inner telescoping pole can be adjusted manually downwardly or upwardly as desired.

A disadvantage with IV poles as they presently exist is that when the detent pin is released, it is possible for the inner telescoping pole to immediately fall to the bottom of the outer pole due to the weight of the bags of IV solution suspended upon the inner pole. This free fall phenomenon due to gravitational acceleration is objectionable and thus subject to criticism.

It has therefore been an objective of the present invention to provide an IV pole which will have sufficient drag as to not freely fall under the weight of bags of IV solution supported by the pole upon releasing its detent pin mechanism.

It has been another objective of the present invention to provide an IV pole which has a variable drag so as to have a controllable rate of fall under the weight of bags of IV solution supported by the pole.

SUMMARY OF THE INVENTION

These objectives are achieved by the present invention by providing an IV pole that includes an interior drag brake which selectively prevents downward movement or allows downward movement of the pole and associated bags of IV solution due to gravitational acceleration.

The IV pole includes a first pole member, and at least a second pole member which telescopes into and out of the first pole member. The second pole member includes on its lower end an O-ring encircling the end, and a nylon split collar encircling the O-ring. The nylon split collar generates a sufficient frictional force against the inner diameter of the first pole member such that the second pole member will not move downwardly with respect to the first pole member under the weight of the bags of solution supported by the second pole member, or alternatively a sufficient frictional force so as to cause the second pole member to move downwardly with a predetermined controlled rate of descent.

The nylon split collar is urged against the inner diameter of the first pole member by the O-ring, thus preventing the nylon split collar from taking a permanent set which would cause it to lose its holding efficiency over time.

The interior drag brake is a spool having a circumferential groove, an O-ring disposed in the groove, and a nylon split collar encircling the O-ring. The spool is adapted to be secured to the end of a tube or rod. The depth of the groove can be varied to completely prevent free fall, or to allow a controlled rate of descent of the pole.

In another embodiment, the IV pole comprises a first pole member, at least a second pole member operable to telescope into and out of the first pole member, a seal disposed between the first and second pole members and operable to create an air cushion beneath the second pole member and within the first pole member, and a valve disposed in the first pole member for bleeding off air between the first and second pole members, whereby the second pole member has a predetermined or selectively controllable rate of descent with respect to the first pole member. The seal can be either an O-ring seal, a Quad-Ring® seal or a lip seal, and the valve is preferably a needle valve.

One advantage of the present invention is that an IV pole is provided which will not freely fall under the weight of bags of solution supported by the pole when the pole is released by its detent pin mechanism.

Another advantage of the present invention is that an IV pole has been provided which incorporates a variable interior drag brake therein thereby providing a controlled rate of fall of the pole under the weight of bags of IV solution.

Yet another advantage of the present invention is that an IV pole has been provided which incorporates an interior drag brake therein, which drag brake has a predictable holding efficiency and operation over a long period of time.

These and other objectives and advantages of the present invention will become more readily apparent during the following detailed description taken in conjunction with the drawings herein, in which:

BRIEF DESCRIPTION OF THE DRAWINGS

FIG. 1 is a side elevational view, partially broken away, of the IV pole of the present invention;

FIG. 2 is a cross-sectional view taken along lines 2—2 of FIG. 1;

FIG. 3 is a view similar to FIG. 2 illustrating another embodiment of the present invention;

FIG. 4A is an enlarged view of a O-ring seal used in conjunction with the invention of FIG. 3;

FIG. 4B is a view similar to FIG. 4A illustrating a Quad-ring seal; and

FIG. 4C is a view similar to FIGS. 4A–B illustrating a lip seal.

DESCRIPTION OF THE PREFERRED EMBODIMENT

With reference to FIG. 1, there is illustrated an IV pole 10 of the present invention. The IV pole 10 includes an extension 12, a lower pole or tube 14, an upper pole or tube 16, and a pole or rod 18. Rod 18 is operable to telescope into and out of the upper tube 16, while the upper tube 16 is operable to telescope into and out of the lower tube 14. Lower tube 14 telescopes up and down upon the extension 12, but is generally permanently located after adjustment as by pinning the lower tube 14 to the extension 12 via pin 20.

The rod 18 includes hooks 22 for supporting one or more bags of IV solution (not shown) thereon. An upper bushing assembly 24 is mounted to the upper end of the upper tube 16 and includes a knob 26 for manipulating a spring loaded pin 28. The pin 28 is receivable into one of a number of detents 30 spaced along the length of the extension rod 18. Similarly, a lower bushing assembly 32 is mounted to the upper end of the lower tube 14 and includes a knob 34 which is used to withdraw a spring loaded pin 36 from one or more detents 38 along the length of the upper tube 16.

Referring now to FIG. 2, the rod 18, upper tube 16 and lower tube 14 are shown in cross-section, and specifically illustrating the lower ends of rod 18 and upper tube 16. The upper tube 16 has a threaded spool 60 threaded into its lower end. The threaded spool 60 includes a spool portion 62 and a threaded stud portion 64 which threads into the lower end of the upper tube 16. The spool portion 62 includes a diametrically innermost circumferential groove 66 and a diametrically outermost circumferential groove 68 generally wider than the groove 66. The inner groove 66 locates a rubber O-ring 70 therein. The outermost groove 68 locates a nylon split collar 72 therein, the outermost portion 72a of which is urged into contact with the inner diameter 14a of the lower tube 14 by the resiliency of the nylon collar and by the O-ring 70. The spool portion 62 could employ only a single groove with the O-ring 70 disposed therein and the split collar 72 encircling the O-ring 70. Additionally other resilient materials other than nylon can be used for collar 72, for example plastics, etc., with satisfactory results. Therefore the invention is not to be limited to any particular material. Moreover, should it be desired, the collar 72 could be eliminated with the invention employing an O-ring 70 of proper cross-sectional diameter to effect proper friction between O-ring and inner tube diameter. Conversely the O-ring could be eliminated with the invention employing a collar of proper cross-section for frictional purposes. A rubber bumper plug 74 is press fitted into the lower side of the threaded spool 60 to prevent any metal-to-metal contact upon lowering the upper tube 16.

The rod 18 includes on its lower end a spool 80 which is secured to the rod 18 via a cap screw 82 which is countersunk into the spool 80. The spool 80 includes a diametrically innermost circumferential groove 84 which contains an O-ring 86, and a diametrically outermost circumferential groove 88 generally wider than the groove 84 which contains a nylon split collar 90. As with threaded spool 60, spool 80 could employ only a single groove as well. The O-ring 86 urges the outermost portion 90a of the nylon split collar 90 outwardly against the inner diameter 16a of the upper tube 16. A rubber plug 92 is press fitted into the upper end of the threaded spool 60 to prevent metal-to-metal contact between the spool 80 and the threaded portion 64 of spool 60.

In use, knob 26 is pulled outwardly thereby pulling pin 28 against the spring force and free of detent 30. Extension rod 18 remains in its original vertical position, however, as the nylon split collar 90 bearing against the inner diameter 16a of the upper tube 16 prevents the rod 18 from moving downwardly under the influence of the weight of bags of IV solution supported thereon. Rod 18 may be grasped and moved either upwardly or downwardly with ease, however, as the frictional force generated by the split collar 90 is not so great as to be difficult to overcome. Split collar 72 and O-ring 70 function in much the same manner for raising and lowering the upper tube 16 with respect to the tube 14 and for preventing undesired gravity-induced movement therebetween.

Grooves 66 and 84 can be modified to selectively control the friction force between collar 72 and tube 14, and collar 90 and tube 16, respectively. For example, the deeper the grooves the less friction generated and the shallower the grooves the more friction generated. Consequently, if a slow free fall is desired, the rate of descent can be selectively adjusted and controlled.

Referring now to FIG. 3, and with like numbers representing like components, an alternative embodiment of the present invention is illustrated. A four lobed Quad-Ring® seal 100 (registered trademark of and manufactured by Minnesota Rubber and Gasket Company, Minneapolis, Minn.) is disposed in groove 68 of spool 60 and provides a seal between spool 60 and surface 14a of tube 14. An air pocket or cushion 102 is thus formed beneath tube 16 and between tubes 14 and 16. An air passage 104 is located in extension 12 and connects with an air passage 106 in tube 14. A needle valve 108 is disposed in the passage 106 and is adjustable to provide for a selective rate of bleeding off of air from air cushion 102, thereby providing a controlled rate of descent of tube 16 and rod 18 with respect to tube 14.

Similarly, spool 80 has disposed in groove 88 a Quad-Ring® seal 110 for engaging surface 16a of tube 16. There is thereby created an air cushion 112 beneath rod 18 and within tube 16. Tube 16 includes a passage 114 which communicates with air cushion 112. A needle valve 116 is disposed in the passage 114 and is operable to bleed off air from the air cushion 112, thereby providing for a controlled rate of descent of rod 18 with respect to tube 16.

With reference to FIGS. 4A–C, it will be seen that numerous types of seals may be employed between the telescoping poles or rods of an IV pole to provide for sealing to enable the telescoping member to ride downwardly atop an air cushion. For example, in FIG. 4A, a simple O-ring seal 120 is illustrated. In FIG. 4B, the before mentioned four lobed Quad-Ring® seal 122 is illustrated, and finally in FIG. 4C, a lip seal 124 is illustrated, which could be either rubber as in the O-ring and Quad-Ring® seals of FIGS. 4A and 4B, respectively, or felt.

Those skilled in the art will readily recognize numerous adaptations and modifications which can be made to the present invention and which will result in an improved IV pole with interior drag brake, yet without departing from the spirit and scope of the present invention, as all of which will be encompassed by the appended claims and their equivalents. Accordingly, I intend to be limited only by the claims and their equivalents.

What is claimed is:

1. An interior drag brake for use between an inner telescoping tube and an outer telescoping tube, the interior drag brake comprising:

a spool configured to be coupled to the inner telescoping tube, the spool having a circumferential groove therein;

a resilient split collar disposed in said groove, said split collar having an outer diameter friction surface configured to engage a surface of the outer telescoping tube, and means disposed in said groove for urging said split collar outwardly such that said friction surface is adapted to engage the surface of the outer telescoping tube in frictional relation thereto to prevent downward movement due to gravitational acceleration of the inner telescoping tube relative to the outer telescoping tube.

2. The interior drag brake of claim 1 including means for attaching said drag brake to the inner telescoping tube.

3. The interior drag brake of claim 1, wherein the means urging said split collar outward has a first stiffness and the split collar has a second stiffness greater than the first stiffness.

4. The interior drag brake of claim 1, wherein the inner telescoping tube includes a lower end and a spool-receiving aperture formed in the lower end and the spool further includes a threaded stud portion configured to be situated in the spool-receiving aperture of the inner telescoping tube.

5. The interior drag brake of claim 4, wherein the spool further includes a shoulder formed adjacent the threaded stud portion, the shoulder being configured to abut the lower end of the inner telescoping tube.

6. An interior drag brake for use between an inner telescoping tube and an outer telescoping tube, the interior drag brake comprising:

a spool configured to be coupled to the inner telescoping tube, the spool having a diametrically innermost circumferential groove and a diametrically outermost circumferential groove wider than said innermost groove;

an O-ring disposed in said innermost groove; and a plastic split collar disposed in said outermost groove, said split collar having an outer diameter friction surface configured to be able to engage a surface of the outer telescoping tube, said O-ring being operable to urge said friction surface against the surface of the outer telescoping tube in frictional relation thereto to prevent downward movement due to gravitational acceleration of the inner telescoping tube relative to the outer telescoping tube.

7. The interior drag brake of claim 6, wherein the O-ring has a first stiffness and the split collar has a second stiffness greater than the first stiffness.

8. The interior drag brake of claim 6, wherein the inner telescoping tube includes a lower end and a spool-receiving aperture formed in the lower end and the spool further includes a threaded stud portion configured to be situated in the spool-receiving aperture of the inner telescoping tube.

9. The interior drag brake of claim 8, wherein the spool further includes a shoulder formed adjacent the threaded stud portion, the shoulder being configured to abut the lower end of the inner telescoping tube.

10. A drag brake system to be used in a telescoping tube apparatus comprising: at least a first, second, and third telescoping tube;

a first spool coupled to the first telescoping tube, the first spool having a diametrically innermost circumferential groove and a diametrically outermost circumferential groove wider than the innermost groove, a second spool coupled to the second telescoping tube, the second spool having a diametrically innermost circumferential groove and a diametrically outermost groove wider than the innermost groove, a first O-ring disposed in the innermost groove of the first spool, a second O-ring disposed in the innermost groove of the second spool, a first plastic collar disposed in the outermost groove of the first spool, the first collar having an outer surface, the first O-ring being configured to urge the outer surface of the first collar against a surface of the second telescoping tube in frictional relation thereto to prevent downward movement due to gravitational acceleration of the first telescoping tube relative to the second telescoping tube, and a second plastic collar disposed in the outermost groove in the second spool, the second collar having an outer surface, the second O-ring being configured to urge the outer surface of the second collar against a surface of the third telescoping tube in frictional relation thereto to prevent downward movement due to gravitational acceleration of the second telescoping tube relative to the third telescoping tube.

11. The drag brake system of claim 10, wherein the first spool includes a top end facing upwardly away from the second spool and a bottom end facing downwardly toward the second spool, the second spool includes a top end facing upwardly toward the first spool and a bottom end facing downwardly away from the first spool, the top end of the second spool is situated adjacent to the bottom end of the first spool when the first telescoping tube is in a retracted position lying within the second telescoping tube.

12. The drag brake system of claim 10, further comprising a spacer situated between the first and second spools.

13. The drag brake system of claim 12, wherein the second spool includes a top end facing upwardly toward the first spool and an aperture formed in the top end, and the spacer is a rubber plug press fitted into the aperture formed in the second spool.

* * * * *